United States Patent
Wilczynski et al.

(12) 
(10) Patent No.: US 6,303,183 B1
(45) Date of Patent: Oct. 16, 2001

(54) ANTI-MICROBIAL PORCELAIN ENAMEL COATING

(75) Inventors: Michael Wilczynski; Glenn N. Pfendt; James D. Waters, all of Florence, KY (US)

(73) Assignee: AOS Holding Company, Wilmington, DE (US)

( * ) Notice: Subject to any disclaimer, the term of this patent is extended or adjusted under 35 U.S.C. 154(b) by 0 days.

(21) Appl. No.: 09/435,988

(22) Filed: Nov. 8, 1999

(51) Int. Cl.$^7$ .................................................... B05D 5/00
(52) U.S. Cl. .................... 427/193; 427/201; 427/204; 427/205; 427/376.2
(58) Field of Search ................. 427/193, 201, 427/204, 205, 427, 376.2; 501/19; 106/15.05, 18.36; 514/618, 630, 635, 641

(56) References Cited

U.S. PATENT DOCUMENTS

| | | | |
|---|---|---|---|
| 4,849,223 | 7/1989 | Pratt et al. | 424/409 |
| 4,906,466 | 3/1990 | Edwards et al. | 424/78 |
| 5,052,926 | 10/1991 | Kawasaki et al. | 433/49 |
| 5,100,451 | * 3/1992 | Toussaint et al. | |
| 5,147,686 | * 9/1992 | Ichimura et al. | |
| 5,151,122 | 9/1992 | Atsumi et al. | 106/35 |
| 5,187,124 | 2/1993 | Kweon | 501/1 |
| 5,264,250 | * 11/1993 | Steele et al. | |
| 5,266,534 | 11/1993 | Atsumi et al. | 501/1 |
| 5,348,577 | 9/1994 | Atsumi et al. | 106/18.31 |
| 5,421,867 | 6/1995 | Yeager et al. | 106/18.32 |
| 5,562,949 | * 10/1996 | Steele et al. | |
| 5,591,453 | 1/1997 | Ducheyne et al. | 424/484 |
| 5,618,762 | 4/1997 | Shirakawa et al. | 501/1 |
| 5,753,250 | 5/1998 | Hagiwara | 424/405 |
| 5,807,641 | * 9/1998 | Oku et al. | |

FOREIGN PATENT DOCUMENTS

| | | | |
|---|---|---|---|
| 114343A | 3/1987 | (CN) | C04B/33/00 |
| 115381A | 6/1997 | (CN) | C03C/1/00 |
| 0 792 687 A1 | 3/1997 | (EP) | B01J/35/02 |
| 6056470 | 3/1994 | (JP) | C03C/8/14 |
| 6234585 | 8/1994 | (JP) | B01J/35/02 |
| 8100274 | 4/1996 | (JP) | C23D/5/00 |
| 8133919 | 5/1996 | (JP) | A01N/59/16 |
| 8151229 | 6/1996 | (JP) | C03C/8/02 |
| 8310968 | 11/1996 | (JP) | C04B/41/80 |
| 8325080 | 12/1996 | (JP) | C04B/41/80 |
| 8333135 | 12/1996 | (JP) | C03C/8/14 |
| 9-142877 | * 6/1997 | (JP) | |
| 6-16521 | * 1/1999 | (JP) | |

OTHER PUBLICATIONS

MicroFree AMP Overview, DuPont web site, 1996–1997.*
"DuPont Specialty Powders", 1996, 1997 E. I. du Pont de Nemours and Company; "MicroFree™ AMP, DuPont MicroFree™ Antimicrobial Powders"; http://www.dupont.com/powders.

* cited by examiner

Primary Examiner—Fred J. Parker
(74) Attorney, Agent, or Firm—Michael Best & Friedrich LLP

(57) ABSTRACT

An anti-microbial porcelain enamel coating and a method of preparing the coating is provided. The porcelain enamel coating contains an anti-microbial agent having an anti-microbial metal compound such as silver, zinc, or copper disposed on a particulate support. The resulting porcelain enamel coating can be used, for example, as a coating over steel for those appliances and sanitary ware fixtures that could benefit from an increased level of resistance to microbes, mold, bacteria, and fungus.

28 Claims, No Drawings

ANTI-MICROBIAL PORCELAIN ENAMEL COATING

FIELD OF INVENTION

This invention relates to porcelain enamel coatings suitable for applications such as domestic appliances and sanitary ware.

BACKGROUND

Porcelain enamel water contact surfaces are susceptible to the growth of microorganisms, especially when used infrequently. This microorganism growth can lead to problems ranging from offensive appearance and odor to health concerns. On sanitary ware surfaces, for example, bathtubs and sinks, and on stove top ranges, chemicals such as detergent and the like are customarily employed to control bacteria after it has grown. Infrequently utilized water heaters, as in summer houses, contain stagnant water in which microbes may proliferate. Once the bacteria forms, a foul odor may be created. In the case of a water heater containing stagnant water, the foul odor tends to linger until enough water has been used over time to replace the stagnant water with fresh water.

It would be desirable to prevent or mitigate the growth of bacteria on surfaces such as sanitary ware and water heaters while maintaining the protective corrosion resistant properties of the porcelain enamel coating.

SUMMARY OF THE INVENTION

The aim of the invention is to produce a functional anti-microbial, anti-mold, or anti-fungal porcelain enamel coating for use as a groundcoat or covercoat in the manufacture of those home appliances and sanitary ware that may benefit from such a coating.

Materials such as copper and silver exhibit anti-microbial properties. Several patents have been issued that, among other things, describe the anti-microbial effects of silver, copper, and zinc (see, for example U.S. Pat. No. 5,147,686 to Ichimura and U.S. Pat. No. 4,906,466 to Edwards).

Silver compounds have been described for use as glaze additive. For example, Japanese Publication 08333135 describes a sintered and crushed mixture of silver phosphate and kaolinite silicate which is said to impart antibacterial properties to the glaze. Also, silver compounds have been applied to the surface of baked enamel. For example, Japanese Publication 8100274 mentions a glaze containing borosilicate glass and a silver salt or a chromium salt which is coated and baked on the surface of baked enamel.

In attempting to produce an anti microbial porcelain enamel coating, one must not lose sight of the primary function of a porcelain enamel coating, which is to protect the substrate to which it is applied. Hence, modifying the porcelain enamel to obtain additional beneficial properties such as anti-microbial properties, requires a balance to ensure the corrosion resistant properties, adhesion properties or other desirable coating properties are not adversely affected in order to achieve anti-microbial properties.

Also, many types of additives would be destroyed in the milling and firing conditions employed in the manufacture of porcelain enamel. For instance, applying raw metal in a porcelain enamel tends to give a reducing effect and tends to cause problems with color stability. In addition, raw metal tends to float to the surface giving the enamel an undesirable sheen.

It has been found that anti-microbial porcelain enamel coatings may be successfully prepared according to the invention.

The invention provides a process for the preparation of an anti-microbial porcelain enamel coating. Generally, this process comprises incorporating an anti-microbial agent into a porcelain enamel composition, wherein the anti-microbial agent includes an anti-microbial metal disposed on a particulate support. The anti-microbial metal is silver, zinc, copper or mixtures thereof. The invention also provides an anti-microbial porcelain enamel coating prepared by the above process.

A more specific process for the preparation of the anti-microbial porcelain enamel coating comprises adding an anti-microbial agent to a glass frit or to a slip to form a mixture; applying the mixture to a substrate; and curing the mixture. The anti-microbial agent includes an anti-microbial metal selected from the group consisting of silver, zinc, copper and mixtures thereof disposed on a particulate support. The anti-microbial agent is added in an amount sufficient to provide anti-microbial properties to the coating; preferably, at least about 1 weight percent based on the total weight of the mixture. The anti-microbial agent is preferably selected from the group consisting of silver coated zinc oxide; copper coated zinc oxide; silver and zinc silicate coated titanium dioxide; silver, copper oxide, and zinc silicate coated titanium dioxide; and silver coated titanium dioxide. The mixture is preferably applied to a metal substrate; and the coated substrate is then fired at a temperature from about 1400° F. to about 1700° F. Thus, the anti-microbial agent is preferably incorporated into the porcelain enamel composition prior to curing the porcelain enamel composition.

The invention also provides an anti-microbial porcelain enamel coating comprising a porcelain enamel composition, and an anti-microbial agent dispersed throughout the porcelain enamel composition and present in an amount effective to provide anti-microbial properties. The anti-microbial agent comprises silver, zinc, copper or mixtures thereof disposed on a particulate support.

Anti-microbial porcelain enamel coatings of the invention may offer increased protection from bacteria (such as escherichia coli, pseudomonas aeruginosa, klebsiella pneumonia, staphylococcus aureus) and fungus (such as mold-aspergillis niger, yeast-candida albicans).

The resulting porcelain enamel coating may be useful in applications such as food contact surfaces, water contact surfaces, water heaters, water storage tanks, range tops, barbecues, and sanitary ware such as bathtubs and sinks.

Other features and advantages of the invention will become apparent to those skilled in the art upon review of the following Detailed Description and claims.

Before embodiments in the invention are explained in detail, it is to be understood that the invention is not limited in its application to the details of the composition or concentration of components, or to the steps or acts set forth in the following description. The invention is capable of other embodiments and of being practiced or being carried out in various ways. Also, it is understood that the phraseology and terminology used herein is for the purpose of description and should not be regarded as limiting.

DETAILED DESCRIPTION OF THE INVENTION

The present invention is an anti-microbial porcelain enamel coating which inhibits the growth of microorganisms and a process for making same.

The anti-microbial porcelain enamel coating generally comprises a porcelain enamel composition and an antimicrobial agent having an anti-microbial metal disposed on a particulate support. Preferably, the anti-microbial agent is dispersed throughout the porcelain enamel composition. The anti-microbial agent should be present in an amount sufficient to provide the desired anti-microbial properties to the porcelain enamel coating. This may be achieved, for example, by adding the anti-microbial agent to the porcelain enamel coating in an amount of at least about 1 weight percent, based on the total weight of the porcelain enamel composition and the anti-microbial agent; more preferably, at least about 4 weight percent. The level of anti-microbial compounds may be varied depending on the degree of anti-microbial and anti-fungal resistance that is needed. For example, for top coat applications, it may be desirable to add the anti-microbial agent in an amount of at least about 15 weight percent.

The anti-microbial agent should be added in an amount less than that at which the anti-microbial agent substantially inhibits the corrosion resistant or other desirable properties of the porcelain enamel coating. Preferably, the anti-microbial agent constitutes at most about 25 weight percent; more preferably, at most about 10 weight percent; most preferably at most about 4 weight percent based on the total weight of the porcelain enamel composition and the anti-microbial agent. For top coat applications higher concentrations of anti-microbial agent may be employed.

The anti-microbial metal, which constitutes part of the anti-microbial agent, is metallic copper (Cu), silver (Ag), zinc (Zn), or any mixture or alloy of these metals. Preferably, the anti-microbial metal includes silver. In anti-microbial compositions according to the invention, the silver is preferably present in the metallic form, optionally as an admixture or alloy with another metal. The anti-microbial agents preferably contain from 0.1 to 3.0% by weight anti-microbial metal, balance particulate support. More preferably, from 0.2 to 2.0% by weight anti-microbial metal.

Suitable particulate supports for use in the anti-microbial agent include, for example, calcium hydroxyapatite; barium sulfate; or an oxide of titanium, magnesium, aluminum, zinc, silicon, cerium, zirconium, hafnium, niobium or tantalum. Titanium dioxide ($TiO_2$), barium sulfate ($BaSO_4$), and zinc oxide (ZnO) are preferred; titanium dioxide and zinc oxide are the most preferred.

The particle size of the particulate support should be smaller than the desired coating thickness; preferably less than about 1.5 microns. Although any combination of copper, silver and zinc may be disposed on any combination of the particulate supports described above, particularly preferred anti-microbial agents include silver coated zinc oxide; copper coated zinc oxide; silver and zinc silicate coated titanium dioxide; silver, copper oxide, and zinc silicate coated titanium dioxide; and silver coated titanium dioxide.

Such anti-microbial agents and their particulate support materials may be made, for example, as described in U.S. Pat. Nos. 4,849,223 and 5,147,686; and European Patent No. EP0792687A1; which are herein fully incorporated by reference. Typically, these anti-microbial agents are obtained by supporting at least one anti-microbial metal of copper, zinc, silver or mixtures or alloys thereof on the surface of a particulate support by methods such as electroless plating, vapor deposition, compression mixing, mixing and reducing, and thermal decomposition. Preferred anti microbial agents are available as anti-microbial powders from E. I. DuPont de Nemours and Company.

Turning now to the process of making the porcelain enamel coating, typically a frit and any mill additions are ground and mixed with water to make a slip. The slip is then applied to a substrate and fired at a temperature of approximately 1400–1700° F. (760–925° C.). The mixture of flit and mill additions other than the anti-microbial agent is referred to herein as the "porcelain enamel composition." Unless otherwise indicated, the weight percents given herein are based on the total weight of the porcelain enamel composition plus the anti-microbial agent, excluding water from the slip.

Customarily, porcelain enamel frits primarily contain some type of glass. Frits generally include some combination of silica, soda ash and borax in addition to metal oxides or ceramic mineral compounds, such as zircon. Enamels are customarily boro-silicate glasses containing alkali metals. The glass frit used in this composition may be produced by discharging molten enamel glass from a smelter into tubs of water or onto water cooled rollers. Preferably, the porcelain enamel composition is predominantly a borosilicate. The frit composition can vary widely depending on the final application and use of the coating.

Mill additions, such as suspending agents (for example, clay), electrolytes, refractories, colors and opacifiers, and bisque strengtheners may be employed as is customary and well-known in the field of porcelain enamel coating production. Adhesion promoters are customarily added to the frit. Typical adhesion promoters include metal oxides such as cobalt oxide (CoO) and nickel oxide (NiO).

The selected minerals are ground to the desired fineness. This is customarily carried out in a ball mill to reduce the frit to a predetermined particle size for application to a component. The grinding may be carried out wet or dry, however, wet grinding with water as the suspending medium is most typical.

The preferred fineness varies depending on the application. The industry standard is approximately 5–10% retained on a 200 Mesh for groundcoats, and 1–4% retained on a 200 Mesh for covercoats. Larger particle sizes or increased coarseness may be desired to avoid defects in the enamel when it is to be applied to steel exhibiting strain lines. Particles tend to be coarser in applications requiring a thick porcelain enamel coating, such as a water heater. Smaller or finer particle sizes may be preferred, for example, for aesthetic purposes such as color. Finer particle sizes may also be appropriate with thinner coatings, such as on bathtubs or ranges. Preferably, the slip is ground to a fineness of between 1% and 10% retained on a standard 200 Mesh sieve.

Typically, any mill additions are added upon commencement of grinding. However, the anti-microbial agent mill addition may be added before, during or after grinding.

Effective anti-microbial porcelain enamel coatings may be obtained via several methods of preparation and application. The method of application is not critical and the coating may be applied to the substrate either wet or dry. Wet applications are preferred and conventional methods include dipping, flow coating, or spraying. The most typical method of application is spraying, for example, with an air pressure assisted spray gun.

The anti-microbial composition may be applied as a coating or layer on a substrate or may be impregnated into the surface layer. When applied, the coating may extend over substantially the entire surface of the substrate or may be applied to a portion of the surface, which may include the exterior and/or the interior surface depending on where the protective properties are required.

In one method, anti-microbial agent is dispersed throughout the slip using a high speed mixer at about 1 to 10 parts per 100 parts of frit; preferably between about 2 and 4 parts per 100 parts of frit. The slip is then applied to the substrate via conventional methods and fired (cured) to produce an anti-microbial enamel coating over steel.

Alternatively, the metal substrate may contain an existing base coat of porcelain enamel onto which the antibacterial porcelain enamel coating is applied. For example, the above slip composition may be applied as such a top coat. The anti-microbial agent may be dispersed throughout the slip at about 15 to 25 parts per 100 parts of white frit, then applied over an existing porcelain enamel coating as a thin top coat, at 10 to 25 percent of normal base coat application.

In another method, anti-microbial agents such as those mentioned herein are mixed in water and applied as a dust coat on top of an uncured porcelain enamel coating. In this process a porcelain enamel composition is applied to a substrate; an anti-microbial agent is applied to the substrate to form a coated substrate; and the coated substrate is fired.

The anti-microbial porcelain enamel coating described herein is preferably applied to a metal substrate. Most preferably, the substrate is a metal such as a steel, iron or aluminum. Steel substrates include items manufactured for food contact surfaces such as stoves, ranges and grills, and water contact surfaces such as sinks, bathtubs, water heaters, and water storage tanks.

After applying the slip to the substrate, the coated substrate may be dried to remove any water, thereby minimizing outgassing in the coating during the curing process. This drying is typically carried out in air at a temperature at about 300° F.

Turning now to firing or curing, the firing should be carried out at a temperature above that at which glass forms. The firing temperature is preferably at least about 1400° F. (760° C.) more preferably at least about 1450° F. (785° C.); and most preferably at least about 1500° F. (815° C.). When applying the porcelain enamel to a metal substrate, the firing temperature should be below that at which the metal begins to melt or deform. Preferably, the firing temperature is less than about 1700° F. (925° C.); more preferably, less than about 1650° F. (895° C.). Temperatures on the order of approximately 1400–1700° F. (760–925° C.) are typically suitable to permit the frit to melt and fuse to the metal and may be achieved, for example, in an enameling kiln.

The result is an anti-microbial porcelain enamel coating which should be thick enough to provide the desired substrate protection. Preferably, the curing coating is at least about 3 mils (76 microns) thick. (1 mil=0.001 inch=25.3 microns.) Thinner coatings, on the order of at least about 3 mils or at least about 5 mils (127 microns), are suitable for applications such as range tops and bathtubs. Thicker coatings, on the order of at least about 10 mils (254 microns), are better suited in applications such as water heaters. An anti-microbial porcelain enamel coating having a thickness of less than about 15 mils (376 microns) is typical.

EXAMPLE

A porcelain enamel coating is prepared with a slip having the following formula:

| Material | Parts |
|---|---|
| Glass frit | 100 |
| Quartz | 3 |
| Clay | 5 |
| Potassuim Carbonate | 0.15 |

-continued

| Material | Parts |
|---|---|
| Sodium Aluminate | 0.1 |
| Bentonite | 0.35 |
| Potassium Nitrate | 0.1 |
| Titanium Dioxide | 2.5 |
| Water | 40 |

The above ingredients are placed in a ball mill, and ground to a wet slurry (known as a slip). The slip is ground to fineness of between 1% and 10% retained on a standard 200 Mesh sieve.

To this slip is added 4 weight percent (4.45 parts per 100 parts of frit) of an anti-microbial agent made of silver coated zinc oxide. The anti-microbial agent is dispersed throughout the slip using a high speed mixer.

After mixing all of the ingredients together, the coating mixture is applied to a groundcoat surface (sheet steel substrate upon which a porcelain enamel groundcoat has already been applied and cured) by spraying and fired at a temperature of 1500° F.

The resulting coating had a total thickness of 8 (4 groundcoat and 4 covercoat) mils (203 microns) and was tested for anti-microbial activity by using a modified AATCC test method 100-1993. The following results were obtained:

|  | Control | Test |
|---|---|---|
| Weight % Antimicrobial Agent | 0% | 4% |
| 8 hours | 21.4% Reduction in *Staphylococcus Aureus* 0.105 Log Reduction | 49.3% Reduction in *Staphylococcus Aureus* 0.295 Log Reduction |
| 24 hours | 32.9% Reduction in *Staphylococcus Aureus* 0.173 Log Reduction | 70.7% Reduction in *Staphylococcus Aureus* 0.533 Log Reduction |

What is claimed is:

1. A process for forming an anti-microbial porcelain enamel coating on a metal substrate, the process comprising:
    (a) incorporating an anti-microbial agent into a porcelain enamel composition, the anti-microbial agent comprising an anti-microbial metal disposed on a particulate support, wherein the anti-microbial metal is selected from the group consisting of silver, zinc, cooper, and alloys and mixtures thereof;
    (b) applying the composition of step (a) to a metal substrate; and
    (c) firing the substrate of step (b) at a temperature of at least about 1100° F. and less than about 1700° F.

2. The process of claim 1 wherein the anti-microbial agent is dispersed throughout the porcelain enamel composition.

3. The process of claim 1 wherein the anti-microbial agent constitutes at least about 1 weight percent of the coating, based on the total weight of the anti-microbial agent and the porcelain enamel composition.

4. The process of claim 1 wherein the anti-microbial agent constitutes at most about 10 weight percent of the coating, based on the total weight of the anti-microbial agent and the porcelain enamel composition.

5. The process of claim 1 wherein the particulate support comprises calcium hydroxyapatite; barium sulfate; or an oxide of titanium, magnesium, aluminum, zinc, silicon, cerium, zirconium, hafnium, niobium or tantalum.

6. The process of claim 5 wherein the particulate support comprises titanium dioxide ($TiO_2$), barium sulfate ($BaSO_4$), or zinc oxide (ZnO).

7. The process of claim 1 wherein the particulate support comprises titanium dioxide ($TiO_2$).

8. The process of claim 1 wherein the anti-microbial agent is selected from the group consisting of silver coated zinc oxide; copper coated zinc oxide; silver and zinc silicate coated titanium dioxide; silver, copper oxide, and zinc silicate coated titanium dioxide; and silver coated titanium dioxide.

9. The process of claim 1 wherein the anti-microbial porcelain enamel coating has a thickness of less than about 15 mils (376 microns).

10. The process of claim 1 wherein the porcelain enamel composition is predominantly a borosilicate.

11. The method of claim 5 wherein the particulate support comprises ZnO.

12. The process of claim 1, wherein firing the substrate of step (b) occurs at a temperature of at least 1400° F. and less than about 1700° F.

13. A process for forming an anti-microbial porcelain enamel coating on a metal substrate, the process comprising:

adding an anti-microbial agent to a glass frit or to a slip to form a mixture, the anti-microbial agent comprising an anti-microbial metal disposed on a particulate support, the anti-microbial metal being selected from the group consisting of silver, zinc, copper and alloys and mixtures thereof;

applying the mixture to a metal substrate; and firing the substrate having the mixture thereon at temperature of at least about 1400° F. (760° C.) and less than about 1700° F. (925° C.).

14. The process of claim 13 wherein the substrate comprises a steel.

15. The process of claim 13 wherein the substrate contains a base coat of a porcelain enamel prior to applying the mixture.

16. The process of claim 13 wherein the substrate is a water heater.

17. The process of claim 13 wherein the substrate is a bathtub, a sink or a water storage tank.

18. The process of claim 13 further comprising the step of grinding the glass frit, wherein the anti-microbial agent is added to the glass frit before, during or after grinding.

19. The process of claim 13 wherein the particulate support comprises calcium hydroxyapatite; barium sulfate; or an oxide of titanium, magnesium, aluminum, zinc, silicon, cerium, zirconium, hafnium, niobium or tantalum.

20. The process of claim 19 wherein the particulate support comprises titanium dioxide ($TiO_2$), barium sulfate ($BaSO_4$), or zinc oxide (ZnO).

21. The process of claim 13 wherein the anti-microbial agent is selected from the group consisting of silver coated oxide; copper coated zinc oxide; silver and zinc silicate coated titanium dioxide; silver, copper, and zinc silicate coated titanium dioxide; and silver coated titanium dioxide.

22. A process for the preparation of an anti-microbial porcelain enamel coating, the process comprising:

grinding a glass frit;

adding at least about 1 weight percent of an anti-microbial agent to the glass frit to form a mixture, the weight percent being based on the total weight of the mixture, and the anti-microbial agent being selected from the group consisting of silver coated zinc oxide; copper coated zinc oxide; silver and zinc silicate coated titanium dioxide; silver, copper oxide, and zinc silicate coated titanium dioxide; and silver coated titanium dioxide;

applying the mixture to a metal substrate to form a coated substrate; and firing the coated substrate at a temperature from about 1100° F. to about 1700° F. to form an anti-microbial porcelain enamel coating.

23. A process for the preparation of an anti-microbial porcelain enamel coating, the process comprising:

applying a porcelain enamel composition and an anti-microbial agent to a metal substrate to form a coated substrate, the anti-microbial agent comprising an anti-microbial metal disposed on a particulate support, the anti-microbial metal being selected from the group consisting of silver, zinc, copper and alloys and mixtures thereof; and firing the coated substrate at a temperature of at least about 1400° F. and less than about 1700° F.

24. A process for coating an internal portion of a water heater with an anti-microbial porcelain enamel coating, the process comprising:

incorporating an anti-microbial agent into a porcelain enamel composition to form an anti-microbial mixture, the anti-microbial agent comprising an anti-microbial metal disposed on a particulate support, wherein the anti-microbial metal is selected from the group consisting of silver, zinc, copper and alloys and mixtures thereof; and applying the anti-microbial mixture to the internal portion of the water heater.

25. The process of claim 24, wherein the internal portion of the water heater is metal.

26. The process of claim 24, wherein the internal portion of the water heater is a water storage tank.

27. The process of claim 24, wherein the internal portion of the water heater is a wall of the water heater.

28. The process of claim 24, wherein the internal portion of the water heater is a flue.

* * * * *

UNITED STATES PATENT AND TRADEMARK OFFICE
CERTIFICATE OF CORRECTION

PATENT NO.    : 6,303,183 B1
DATED         : October 16, 2001
INVENTOR(S)   : Michael Wilczynski, Glenn N. Pfendt and James D. Waters It is certified that error appears in the above-identified patent and that said Letters Patent is hereby corrected as shown below:

<u>Column 8,</u>
Line 2, after "coated" insert -- zinc --; and
Line 4, after "copper" and before the comma (,) insert -- oxide --.

Signed and Sealed this

Sixth Day of August, 2002

*Attest:*

*Attesting Officer*

JAMES E. ROGAN
*Director of the United States Patent and Trademark Office*